(12) United States Patent
Nakamura et al.

(10) Patent No.: US 9,327,970 B2
(45) Date of Patent: May 3, 2016

(54) SYNTHESIS GAS AND NANOCARBON PRODUCTION METHOD AND PRODUCTION SYSTEM

(75) Inventors: Satoru Nakamura, Hokkaido (JP); Akio Tada, Hokkaido (JP)

(73) Assignees: THE JAPAN STEEL WORKS, LTD., Tokyo (JP); National Univeristy Corporation Kitami Institute of Technology, Hokkaido (JP)

( * ) Notice: Subject to any disclaimer, the term of this patent is extended or adjusted under 35 U.S.C. 154(b) by 177 days.

(21) Appl. No.: 14/004,321

(22) PCT Filed: Mar. 9, 2012

(86) PCT No.: PCT/JP2012/056157
§ 371 (c)(1),
(2), (4) Date: Sep. 10, 2013

(87) PCT Pub. No.: WO2012/124636
PCT Pub. Date: Sep. 20, 2012

(65) Prior Publication Data
US 2014/0005283 A1    Jan. 2, 2014

(30) Foreign Application Priority Data

Mar. 11, 2011   (JP) .................. 2011-053865

(51) Int. Cl.
| | | |
|---|---|---|
| *C07C 1/02* | (2006.01) | |
| *C07C 27/00* | (2006.01) | |
| *C01B 3/26* | (2006.01) | |
| *C10K 3/02* | (2006.01) | |
| *C10K 3/06* | (2006.01) | |
| *C01B 31/02* | (2006.01) | |
| *C01B 31/18* | (2006.01) | |
| *B01J 7/00* | (2006.01) | |
| *C07C 29/151* | (2006.01) | |
| *B01J 38/04* | (2006.01) | |
| *B01J 23/94* | (2006.01) | |
| *B01J 23/745* | (2006.01) | |
| *B01J 23/755* | (2006.01) | |
| *B01J 23/78* | (2006.01) | |
| *B82Y 30/00* | (2011.01) | |
| *B82Y 40/00* | (2011.01) | |
| *B01J 23/80* | (2006.01) | |

(52) U.S. Cl.
CPC ... *C01B 3/26* (2013.01); *B01J 7/00* (2013.01); *B01J 23/745* (2013.01); *B01J 23/755* (2013.01); *B01J 23/78* (2013.01); *B01J 23/94* (2013.01); *B01J 38/04* (2013.01); *B82Y 30/00* (2013.01); *B82Y 40/00* (2013.01); *C01B 31/0206* (2013.01); *C01B 31/18* (2013.01); *C07C 29/1516* (2013.01); *C10K 3/026* (2013.01); *C10K 3/06* (2013.01); *B01J 23/80* (2013.01); *C01B 2203/0277* (2013.01); *C01B 2203/043* (2013.01); *C01B 2203/048* (2013.01); *C01B 2203/0827* (2013.01); *Y02P 20/129* (2015.11); *Y02P 20/584* (2015.11)

(58) Field of Classification Search
CPC ................. B01J 2203/0277; B01J 2203/1041; B01J 2203/1058; B01J 2203/1241; C01B 2203/0475; C01B 31/0206; C01B 31/18; C10G 2/30
USPC .......................................... 518/702; 252/373
See application file for complete search history.

(56) References Cited

U.S. PATENT DOCUMENTS

| | | | |
|---|---|---|---|
| 5,767,165 A | 6/1998 | Steinberg et al. | |
| 6,315,977 B1 | 11/2001 | Cantacuzene | |
| 2005/0063900 A1* | 3/2005 | Wang ..................... | B01J 23/002 423/658.2 |
| 2006/0257310 A1 | 11/2006 | Tada et al. | |
| 2008/0181845 A1 | 7/2008 | Zhu et al. | |
| 2008/0263954 A1 | 10/2008 | Hammel et al. | |
| 2009/0158662 A1 | 6/2009 | Towler | |
| 2010/0305221 A1 | 12/2010 | Schunk et al. | |

FOREIGN PATENT DOCUMENTS

| | | |
|---|---|---|
| CN | 101300191 A | 11/2008 |
| CN | 101550356 A | 10/2009 |
| JP | 7-69603 A | 3/1995 |
| JP | 2000-281304 A | 10/2000 |
| JP | 2001-220103 A | 8/2001 |
| JP | 2006-96590 A | 4/2006 |
| JP | 2006-315891 A | 11/2006 |
| JP | 2007-254180 A | 10/2007 |
| JP | 2010-516609 A | 5/2010 |
| JP | 2010-526759 A | 8/2010 |
| WO | 2006/040788 A1 | 4/2006 |
| WO | WO 2009/079681 A1 * | 7/2009 |

OTHER PUBLICATIONS

Takenaka, et al., "Tanji Nickel Shokubaijo ni Methane Bunkai de Sekishutsu shita Carbon Fiber no Co2 ni yoru Gas-ka", Dai 31 Kai Sekiyu Sekiyukagaku Toronkai Koen Yoshi, Nov. 1, 2001, 9 pgs total.
International Search Report dated Apr. 17, 2012 issued in International Application No. PCT/JP2012/056157 (PCT/ISA/210).
Written Opinion dated Apr. 17, 2012 issued in International Application No. PCT/JP2012/056157 (PCT/ISA/237).
Communication from the European Patent Office issued Aug. 21, 2014 in a counterpart European Application No. 12758046.2.

* cited by examiner

*Primary Examiner* — Jafar Parsa
(74) *Attorney, Agent, or Firm* — Sughrue Mion, PLLC (57) ABSTRACT

A synthesis gas and nanocarbon production method has a lower hydrocarbon decomposition step for decomposing lower hydrocarbon to produce hydrogen and nanocarbon, a carbon dioxide reduction step for reacting a part of the nanocarbon produced with carbon dioxide to produce carbon monoxide, and a mixing step for mixing the hydrogen and carbon monoxide produced in a predetermined ratio, thereby nanocarbon and a synthesis gas having a desired gas ratio can be simultaneously produced easily.

13 Claims, 3 Drawing Sheets

SYNTHESIS GAS AND NANOCARBON PRODUCTION METHOD AND PRODUCTION SYSTEM

TECHNICAL FIELD

The present invention relates to a production method and production system for producing nanocarbon and a synthesis gas as a raw material for producing various chemical products or fuels from a lower hydrocarbon such as methane, and carbon dioxide.

BACKGROUND ART

A "synthesis gas production method" as described in PTL 1 is known as a related-art synthesis gas production method. This production method produces a synthesis gas (a mixed gas of carbon monoxide and hydrogen) while minimizing energy necessary for a reaction by optimally combining three reactions of (1) a dry reforming reaction of reacting a hydrocarbon compound mainly rich in methane with carbon dioxide, (2) a steam reforming reaction of reacting the hydrocarbon compound with steam, and (3) an autothermal reaction of reacting the hydrocarbon compound with oxygen.

The reactions (1) to (3) above are specifically reactions shown below. The reactions (1) and (2) are an endothermic reaction, and the reaction (3) is an exothermic reaction.

$$CH_4 + CO_2 \rightarrow 2CO + H_2 + 284 \text{ kJ/mol} \quad (1)$$

$$CH_4 + H_2O \rightarrow CO + 3H_2 + 206 \text{ kL/mol} \quad (2)$$

$$CH_4 + \tfrac{1}{2}O_2 \rightarrow CO + 2H_2 - 35.6 \text{ kJ/mol} \quad (3)$$

It is preferred as raw materials for a chemical product that carbon monoxide and hydrogen in a synthesis gas are present in a proportion of 1:2 (molar ratio). PTL 1 describes an optimized production method by combining the reactions (1) to (3) described above such that a synthesis gas ratio is optimized and energy necessary for a reaction is minimized and by supplementing insufficient energy by utilization of natural energy such as sunlight heat.

In "a method for producing hydrogen and carbon monoxide using methane as a raw material" described in PTL 2, a method for continuously producing hydrogen or carbon monoxide by contacting a natural gas containing methane with a metal oxide containing a rare earth at from 200 to 1,000° C. to react with lattice oxygen, thereby reducing the metal oxide, and then reacting the reaction medium reduced with steam or carbon dioxide is disclosed.

The reaction in PTL 2 is represented by the following formula (4). In this reaction formula, rare earth oxide is expressed as $M_nO_m$ (M is a rare earth element).

X is a stoichiometric coefficient.

$$X.CH_4 + M_nO_m \rightarrow 2X.H_2 + X.CO + M_nO_{m-x} \quad (4)$$

The case that cerium is used as rare earth is represented by the following formula (5).

$$X.CH_4 + CeO_2 \rightarrow 2X.H_2 + X.CO + CeO_{2-x} \quad (5)$$

In the reaction of the formula (5), carbon in methane bonds to oxygen in cerium oxide to generate CO, and additionally hydrogen remained in methane is generated. As a result, CO and $H_2$ that are synthesis gases are produced in a certain ratio. When cerium oxide whose oxygen has been reduced is reacted with $CO_2$ or $H_2O$, the cerium oxide of the initial state can be refreshed as shown in the formulae (6) and (7), and this simultaneously makes it possible to produce CO or $H_2$.

$$CeO_{2-x} + X.CO_2 \rightarrow CeO_2 + X.CO \quad (6)$$

$$CeO_{2-x} + X.H_2O \rightarrow CeO_2 + X.H_2 \quad (7)$$

CITATION LIST

Patent Literature

PTL 1: JP-T-2010-526759 (the term "JP-T" as used herein means a published Japanese translation of a PCT application)
PTL 2: JP-A-7-69603

SUMMARY OF INVENTION

Technical Problem

The related-art lower hydrocarbon decomposition reaction is the processes as described above, and hydrogen and carbon monoxide that are synthesis gases are simultaneously produced. Therefore, to achieve an optimum gas ratio (molar ratio of carbon monoxide and hydrogen) for the production of chemical raw materials, optimization of the reaction conditions such as temperature, pressure and superficial velocity by fine setting is necessary, and separation and refinement of hydrogen and carbon monoxide are further necessary. Thus, the operation is complicated. Additionally, water, carbon monoxide, oxygen and the like that are a by-product and an unreacted gas must be removed. Furthermore, there are disadvantages such that the system efficiency is decreased because the reaction between carbon dioxide and hydrogen produces water and hydrogen is used in an amount more than the amount needed.

The present invention has been made to solve the above problems in the related art, and has an object to provide a production method and a production system that can produce nanocarbon and simultaneously easily obtain synthesis gases in a desired gas ratio, using lower hydrocarbon. The present invention further has an object to provide a production method and a production system that suppress production of water due to waste use of hydrogen.

Solution to Problem

That is, according to a first aspect of the present invention, there is provided a synthesis gas and nanocarbon production method, comprising: a lower hydrocarbon decomposition step of directly decomposing lower hydrocarbon using a catalyst to produce hydrogen and nanocarbon; a carbon dioxide reduction step of reacting a part of the nanocarbon produced in the lower hydrocarbon decomposition step with carbon dioxide to produce carbon monoxide; and a mixing step of mixing the hydrogen produced in the lower hydrocarbon decomposition step and the carbon monoxide produced in the carbon dioxide reduction step in a predetermined ratio to obtain a synthesis gas.

According to a second aspect of the present invention, the synthesis gas and nanocarbon production method according to the first aspect further comprises a synthesis step of subjecting the synthesis gas obtained in the mixing step to a reaction to obtain a synthetic substance.

According to a third aspect of the present invention, in the synthesis gas and nanocarbon production method according to the first or second aspect, wherein the carbon dioxide reduction step includes a catalyst refreshing step of subjecting a part or the whole of the catalyst used in the lower hydrocarbon decomposition step to the reaction between the nanocarbon and the carbon dioxide, and removing a part or the whole of the nanocarbon produced in the lower hydrocarbon decomposition step from the catalyst in conducting the reaction.

According to a fourth aspect of the present invention, in the synthesis gas and nanocarbon production method according to the third aspect, wherein the catalyst refreshed in the catalyst refreshing step is again applied to the lower hydrocarbon decomposition step.

According to a fifth aspect of the present invention, in the synthesis gas and nanocarbon production method according to any one of the first to fourth aspects, wherein the lower hydrocarbon contains methane.

According to a sixth aspect of the present invention, in the synthesis gas and nanocarbon production method according to any one of the first to fifth aspects, wherein the catalyst comprises at least one of nickel and iron, supported on at least one of alumina, silica, magnecia, calcia, hydrotalcite, and carbon.

According to a seventh aspect of the present invention, in the synthesis gas and nanocarbon production method according to any one of the first to sixth aspects, wherein the carbon dioxide is collected from at least one of combustion exhaust gas in the lower hydrocarbon decomposition step, exhaust gas in various industries, and biogas.

According to an eighth aspect of the present invention, in the synthesis gas and nanocarbon production method according to any one of the first to seventh aspects, wherein at least one of lower hydrocarbon and hydrogen is used as a reducing agent in the carbon dioxide reduction step.

According to a ninth aspect of the present invention, in the synthesis gas and nanocarbon production method according to any one of the first to eighth aspects, wherein the lower hydrocarbon decomposition step and the carbon dioxide reduction step are conducted by switching supply of the lower hydrocarbon and supply of the carbon dioxide to the same catalyst.

According to a tenth aspect of the present invention, the synthesis gas and nanocarbon production method according to any one of first to ninth aspects further comprises: a collection step for collecting the nanocarbon produced in the lower hydrocarbon decomposition step, wherein the nanocarbon collected in the collection step is supplied to the carbon dioxide reduction step.

According to an eleventh aspect of the present invention, in the synthesis gas and nanocarbon production method according to the tenth aspect, wherein after pulverizing the nanocarbon collected together with the catalyst in the collection step, high purity carbon and nanocarbon containing high concentration of the catalyst are separated by at least one of specific gravity and magnetism, and the nanocarbon containing high concentration of the catalyst is preferentially supplied to the carbon dioxide reduction step.

According to a twelfth aspect of the present invention, there is provided a synthesis gas and nanocarbon production system, comprising: a lower hydrocarbon decomposition reactor, in which a lower hydrocarbon supply tube for supplying lower hydrocarbon is connected thereto, a catalyst is stored in a space communicated with the lower hydrocarbon supply tube, and the space is a reaction space where the lower hydrocarbon is directly decomposed; a carbon monoxide production reactor, in which a carbon dioxide supply tube for supplying carbon dioxide is connected thereto, nanocarbon is stored in a space communicated with the carbon dioxide supply tube, and the space is a reaction space where the carbon dioxide is reduced to carbon monoxide; and a mixing equipment, which is connected to the lower hydrocarbon decomposition reactor and the carbon monoxide production reactor, and in which the hydrogen produced in the lower hydrocarbon decomposition reactor and the carbon monoxide produced in the carbon monoxide production reactor are mixed.

According to a thirteenth aspect of the present invention, the synthesis gas and nanocarbon production system according to the twelfth aspect further comprises: a heat exchanger for cooling the hydrogen produced in the lower hydrocarbon decomposition reactor; and a waste heat supply tube for supplying heat obtained by the heat exchanger to at least one of the lower hydrocarbon decomposition reactor and the carbon monoxide production reactor.

According to a fourteenth aspect of the present invention, in the synthesis gas and nanocarbon production system according to the twelfth or thirteenth aspect, wherein the lower hydrocarbon decomposition reactor and the carbon monoxide production reactor have a common reaction vessel, and wherein the lower hydrocarbon decomposition reactor and the carbon monoxide production reactor have a switching part configured to switch supply of the lower hydrocarbon and supply of the carbon dioxide in the lower hydrocarbon supply tube and the carbon dioxide supply tube to selectively supply them to the reaction space.

According to a fifteenth aspect of the present invention, the synthesis gas and nanocarbon production system according to any one of the twelfth to fourteenth aspects further comprises: a nanocarbon collection vessel configured to collect the nanocarbon produced in the lower hydrocarbon decomposition reactor; and a nanocarbon transfer tube for transferring the nanocarbon after being collected by the nanocarbon collection vessel to the carbon monoxide production reactor.

According to a sixteenth aspect of the present invention, the synthesis gas and nanocarbon production system according to the fifteenth aspect further comprises: a pulverization part configured to pulverize the catalyst-containing nanocarbon collected by the nanocarbon collection vessel; and a separation part, which is provided at a later step of the pulverization part, and which is configured to separate high purity nanocarbon and nanocarbon containing high concentration of the catalyst, wherein the nanocarbon transfer tube is connected to the selection part so as to transfer the selected nanocarbon containing high concentration of the catalyst.

Advantageous Effects of Invention

The synthesis gas and nanocarbon production method according to the present invention includes a lower hydrocarbon decomposition step of directly decomposing a lower hydrocarbon using a catalyst to produce hydrogen and nanocarbon, a carbon dioxide reduction step of reacting a part of the nanocarbon produced in the lower hydrocarbon decomposition step with carbon dioxide to produce carbon monoxide, and a mixing step of mixing the hydrogen produced in the lower hydrocarbon decomposition step and the carbon monoxide produced in the carbon dioxide reduction step in a predetermined ratio to obtain a synthesis gas. Therefore, nanocarbon and a synthesis gas can be produced from lower hydrocarbon and carbon dioxide. Furthermore, a hydrogen/carbon monoxide ratio in a synthesis gas, which has been difficult to adjust in the related-art method, is easily adjusted to an intended value. Additionally, water by-produced by waste use of hydrogen in the related-art method use can be suppressed from being produced.

The synthesis gas and nanocarbon production system according to the present invention includes a lower hydrocarbon decomposition reactor in which a lower hydrocarbon supply tube for supplying lower hydrocarbon is connected thereto, a catalyst is stored in a space communicated with the lower hydrocarbon supply tube, and the space is a reaction space where the lower hydrocarbon is directly decomposed; a carbon monoxide production reactor in which a carbon dioxide supply tube for supplying carbon dioxide is connected thereto, nanocarbon is stored in a space communicated with the carbon dioxide supply tube, and the space is a reaction space where the carbon dioxide is reduced to carbon monoxide; and a mixing equipment connected to the lower hydrocarbon decomposition reactor and the carbon monoxide production reactor, in which the hydrogen produced in the lower hydrocarbon decomposition reactor and the carbon monoxide produced in the carbon monoxide production reactor are mixed. Therefore, the production system can surely achieve the above-described production method.

DESCRIPTION OF EMBODIMENTS

According to the present invention, lower hydrocarbon is decomposed, hydrogen and nanocarbon are produced by the decomposition, and a synthesis gas is produced from the nanocarbon and carbon dioxide. Hydrogen and carbon monoxide that are components of the synthesis gas are produced by the separate steps, respectively, and then mixed. Therefore, a gas ratio (ratio of carbon monoxide and hydrogen) of the synthesis gas can be optionally and easily adjusted. Nanocarbon other than the nanocarbon used in the carbon dioxide reduction step can be used in various uses as a functional material.

In the related-art synthesis gas production method, water is produced by the reaction between carbon dioxide and hydrogen, thereby hydrogen has been wastefully used. However, the present invention does not require production of water, and can eliminate the waste.

Heat of reaction necessary for the lower hydrocarbon decomposition step and the carbon dioxide reduction step can be obtained from exhaust heat emitted in producing a chemical raw material or a fuel based on the reaction gas produced in the present invention, and exhaust heat from various industries. This can lead to effective utilization of energy. Examples of the exhaust heat from various industries include exhaust heat from factories in steel industry, chemical industry, paper-making industry, pulp industry and the like, and exhaust heat from power generation facility.

According to the present invention, the production method can further include a synthesis step of subjecting the synthesis gas obtained in the mixing step to a reaction to obtain a synthetic substance. The synthetic substance is not limited so long as it is a substance that can be synthesized from hydrogen and carbon monoxide, and examples thereof include methanol, ethanol, DME, mixed alcohol, ethylene glycol, oxalic acid, acetic acid and FT synthetic product (artificial gasoline, kerosene or light oil).

The synthesis gas produced by the present invention uses hydrogen and carbon monoxide in a high temperature state produced in the lower hydrocarbon decomposition step and the carbon dioxide reduction step, and therefore can be obtained in a high temperature state. In the present invention, the synthesis gas is obtained in the course of the reaction process, and hydrogen and carbon monoxide before the synthesis reaction have a temperature relatively near the synthesis reaction temperature. Input of energy necessary for a reaction can be reduced by producing methanol or the like using the high temperature synthesis gas.

In the case that a temperature of hydrogen produced in the lower hydrocarbon decomposition step is too high, the hydrogen may be cooled by a heat exchanger or the like as necessary, and then applied to the production of a synthesis gas. Heat obtained by heat exchange in cooling can be utilized as, for example, heat source for the lower hydrocarbon decomposition step and/or the carbon dioxide reduction step.

According to the present invention, the nanocarbon produced in the lower hydrocarbon decomposition step is applied to the carbon dioxide reduction step in a state mixed with a catalyst, thereby oxidizing the nanocarbon by carbon dioxide. As a result, a catalyst such as a catalyst metal, and a carrier supporting the catalyst become a solid residue, and the solid residue can be again used as a catalyst for lower hydrocarbon decomposition. Specifically, in this case, the carbon dioxide reduction step includes a catalyst refreshing step comprising refreshing and activation operation of a catalyst.

Representative lower hydrocarbon used in the lower hydrocarbon decomposition step is methane. However, the lower hydrocarbon is not limited to methane, and ethane, propane, butane, ethylene, propylene, butylene and the like can be used. Mixed gases of those may be used. Representative examples of the mixed gas include gases comprising methane or ethane as a main component. In the case of the mixed gas comprising methane as a main component, the mixed gas includes natural gas containing 80 vol % or more of methane.

Origin of the lower hydrocarbon is not particularly limited. Lower hydrocarbon obtained as natural gas, city gas 13A, boil off gas or biogas, and lower hydrocarbon obtained by chemical synthesis can be used.

The catalyst used in the lower hydrocarbon decomposition step can be any catalyst so long as it can decompose lower hydrocarbon to produce hydrogen and nanocarbon, and is not limited to a specific catalyst in the present invention. A catalyst comprising at least one of alumina, silica, magnesia, calcia, hydrotalcite and carbon as a carrier, and at least one of nickel and iron as a catalyst material, supported on the carrier is particularly exemplified. In this case, the amount of at least one of nickel and iron supported is desirably 30 mass % or more.

The catalyst may be constituted of only the catalyst material without using a carrier.

The carbon dioxide used in the carbon dioxide reduction step of the present invention can use carbon dioxide collected from combustion exhaust gas in the lower hydrocarbon decomposition step and/or the carbon dioxide reduction step. This can reduce the amount of carbon dioxide finally emitted. Furthermore, carbon dioxide is collected from exhaust gas in various industries, or biogas, and the carbon dioxide can be effectively utilized.

At least one of methane and hydrogen can be used as a reducing agent in the carbon dioxide reduction step. This promotes the reaction in the carbon dioxide reduction step.

The lower hydrocarbon decomposition step and the carbon dioxide reduction step can be conducted by switching supply of the lower hydrocarbon and supply of the carbon dioxide to the same catalyst. For example, this embodiment can be achieved by providing a switching part where a reaction space in the lower hydrocarbon decomposition reactor and a reaction space in the carbon monoxide production reactor are common, and supply of the lower hydrocarbon and supply of the carbon dioxide are switched to selectively supply either of those to the reaction space. Two steps are conducted in one reaction space, and therefore facility becomes compact.

The switching may be conducted every predetermined time, or may be conducted based on reaction state (decrease in reaction efficiency, and the like). The switching can be conducted manually, or may be automatically conducted by, for example, a control part judging count of time and reaction state.

In supplying a part of the nanocarbon produced in the lower hydrocarbon decomposition step to the carbon dioxide reduction step, a collection equipment is provided and the nanocarbon produced can be collected by the collection equipment. Constitution of the collection equipment is not particularly limited in the present invention, and appropriate constitution and method can be applied. For example, a method by overflow from a reaction vessel, a method in which an extraction port is provided at a lower part of a reaction vessel and nanocarbon is extracted from the extraction port, and the like can be applied as the collection equipment.

Furthermore, a pulverization part for pulverizing the nanocarbon collected and a selection part for selecting nanocarbon containing high concentration of a catalyst in the carbon pulverized may be provided at a downstream side of the collection step, and the carbon containing high concentration of a catalyst may be preferentially supplied to the carbon monoxide production reactor. The selection part can be, for example, a gravity concentration part of conducting selection by specific gravity and a magnetic separation part of conducting separation by magnetism. The amount of the catalyst refreshed is increased by the above selection, and thereby the amount of the catalyst replenished in the lower hydrocarbon decomposition step can be suppressed. The pulverization part and selection part described above are not limited to specific parts in the present invention.

Embodiment 1

One embodiment of the synthesis gas and nanocarbon production system in the present invention is described below based on FIG. 1. This embodiment produces nanocarbon and a synthesis gas by operating a lower hydrocarbon direct decomposition apparatus and a carbon monoxide production reactor in parallel. This embodiment is described on the assumption that methane is used as lower hydrocarbon. However, the type of lower hydrocarbon is not limited to methane in the present invention.

The production system of the present invention includes a lower hydrocarbon decomposition reactor 10, a carbon monoxide production reactor 30, and a mixing equipment 50.

The lower hydrocarbon decomposition reactor 10 comprises a reaction vessel 11 in which a catalyst 13 for directly decomposing methane is stored, and a furnace 12 for heating the inside of the reaction vessel 11 by surrounding the reaction vessel 11. The inside of the reaction vessel 11 constitutes a reaction space that directly decomposes methane. Examples of the catalyst 13 include a catalyst containing at least one of alumina, silica, magnesia, calcia and hydrotalcite, and at least one of nickel and iron supported thereon in an amount of 30 mass % or more, and a catalyst constituted of only a catalyst material such as at least one of nickel and iron, without using a carrier.

A lower hydrocarbon supply tube 20 for supplying methane as a raw material to the reaction vessel 11, and a production gas transfer tube 14 for transferring production gas produced in the reaction vessel are connected to the reaction vessel 11. The lower hydrocarbon supply tube 20 has a junction on the way to the reaction vessel 11, and a fuel supply tube 21 described hereinafter is connected to the junction. This embodiment is based on the assumption that a part of raw material methane is used as a fuel for heating a furnace, but hydrocarbon different from the raw material may be used as a fuel. In this case, the fuel supply tube is not branched from the lower hydrocarbon supply tube, but a fuel supply tube is separately provided.

PSA (pressure swing adsorption) 25 for collecting methane from an production gas through a heat exchanger 24 for cooling the production gas is connected to the production gas transfer tube 14. A return flow tube 26 for transferring methane separated and collected, and a hydrogen transfer tube 14a for transferring hydrogen separated from the production gas are connected to the PSA 25. Another end of the hydrogen transfer tube 14a is connected to a mixing equipment 50. The return flow tube 26 joins the fuel supply tube 21 through the heat exchanger 24.

This embodiment is based on the assumption that methane collected by the PSA 25 is heated by heat collected by the heat exchanger 24, but is not limited to the above constitution if the heat of the production gas can be utilized as a heat source or the like in the lower hydrocarbon decomposition step and/or the carbon dioxide reduction step.

A nanocarbon collection vessel 42 for extracting the nanocarbon in a state mixed with a catalyst is provided in the reaction vessel 11. Constitution of the nanocarbon collection vessel 42 is not particularly limited, and may be a constitution that nanocarbon is overflown from the reaction vessel 11 or is extracted by providing an extraction port at a lower part of the reaction vessel 11. A nanocarbon-catalyst mixture transfer tube 43 is connected to the nanocarbon collection vessel 42, and the nanocarbon-catalyst mixture transfer tube 43 is connected to a reaction vessel 31 described hereinafter. The nanocarbon-catalyst mixture transfer tube 43 corresponds to the nanocarbon transfer tube of the present invention.

The catalyst-containing nanocarbon collected in the nanocarbon collection vessel 42 is pulverized and then separated into high purity nanocarbon and nanocarbon containing high concentration of a catalyst, and the separated nanocarbon containing high concentration of a catalyst may be transferred to the reaction vessel 31 through the nanocarbon-catalyst mixture transfer tube 43. The pulverization is conducted in the pulverization part, and the separation can be conducted in a separation part by gravity concentration or magnetic separation.

The fuel supply tube 21 for supplying methane as a fuel to the furnace 12 and a carbon dioxide supply tube 23 for supplying carbon dioxide in exhaust gas generated by combustion in the furnace 12 to the carbon monoxide production reactor 30 are connected to the furnace 12, as described before.

The carbon monoxide production reactor 30 includes the reaction vessel 31 in which nanocarbon is stored in a state mixed with a catalyst, and a furnace 32 for heating the inside of the reaction vessel 31 by surrounding the reaction vessel 31. The inside of the reaction vessel 31 corresponds to a reaction space that produces carbon monoxide by the reaction between nanocarbon and a catalyst. The above-described carbon dioxide supply tube 23 and nanocarbon-catalyst mixture transfer tube 43 are connected to the reaction vessel 31. A carbon monoxide transfer tube 34 for transferring carbon monoxide produced in the reaction vessel 31 to the mixing equipment 50 is connected to the reaction vessel 31.

A fuel supply tube 22 for supplying methane as a fuel to the furnace 32, and a carbon dioxide supply tube 35 for transferring carbon dioxide in exhaust gas generated by combustion in the furnace 32 to the carbon dioxide supply tube 23 are connected to the furnace 32.

The hydrogen transfer tube 14a and the carbon monoxide transfer tube 34 are connected to the mixing equipment 50, and hydrogen and carbon monoxide are supplied to the mixing equipment 50. Furthermore, a synthesis gas transfer tube 51 for transferring outside a synthesis gas produced, and an excess hydrogen transfer tube 52 for transferring outside excess hydrogen are connected to the mixing equipment 50. A mixing ratio of hydrogen and carbon monoxide can be arbitrarily adjusted in the mixing equipment 50 by adjusting an amount of hydrogen transferred outside. The amount of hydrogen transferred outside can be adjusted by, for example, a flow rate regulation valve.

Action of this embodiment is described below.

A catalyst 13 is stored in the reaction vessel 11 of the lower hydrocarbon decomposition reactor 10. Methane is supplied to the reaction vessel 11 through the lower hydrocarbon supply tube 20.

The reaction vessel 11 is heated by the furnace 12 using methane as a fuel supplied through the fuel supply tube 21. In this case, carbon dioxide in a combustion exhaust gas discharged from the furnace 12 is supplied to the reaction vessel 31 of the carbon monoxide production reactor 30 through the carbon dioxide supply tube 23.

When methane is supplied to the reaction vessel 11 in the state that the reaction vessel 11 is heated to a predetermined temperature, nanocarbon and hydrogen are produced by the reaction between the catalyst 13 and methane. Temperature and pressure in this case are not particularly limited, and can be appropriately determined considering a conversion of methane, and the like.

Production gas produced in the reaction vessel 11 is discharged outside the reaction vessel 11 through the production gas transfer tube 14, and transferred to the PSA 25 through the heat exchanger 24.

Unreacted methane and hydrogen are separated from the production gas by the PSA 25. The methane collected is transferred to the fuel supply tube 21 by the return flow tube 26 through the heat exchanger 24, and can be used again as a fuel. Heat exchange between the production gas and the methane collected is conducted in the heat exchanger 24, the production gas is cooled, and at the same time, the methane collected is heated. The heating of the methane collected increases energy efficiency as preheating of a fuel.

On the other hand, the hydrogen separated by PSA 25 is transferred to the mixing equipment 50 through the hydrogen transfer tube 14a.

Nanocarbon is produced by the decomposition reaction in the reaction vessel 11. The nanocarbon is extracted together with a catalyst outside the reaction vessel 11 by the nanocarbon collection vessel 42. Necessary amount of nanocarbon is separated and can be used as a functional material or the like. A part of nanocarbon and the catalyst are transferred to the reaction vessel 31 through the nanocarbon-catalyst mixture transfer tube 43. In the present invention, only nanocarbon may be transferred to the reaction vessel 31.

A nanocarbon-adhered catalyst 33 is stored in the reaction vessel 31 of the carbon monoxide production reactor 30. Carbon dioxide is supplied to the reaction vessel 31 of the carbon monoxide production reactor 30 through the carbon dioxide supply tube 23, and the catalyst-containing nanocarbon is supplied to the reaction vessel 31 through the nanocarbon-catalyst mixture transfer tube 43. The reaction vessel 31 is heated by the furnace 32 using methane as a fuel supplied through the fuel supply tube 22. In this case, the carbon dioxide in the combustion exhaust gas discharged from the furnace 32 is supplied to the reaction vessel 31 through the carbon dioxide supply tube 35 and then though the carbon dioxide supply tube 23.

Nanocarbon and carbon dioxide are reacted at a predetermined temperature under a predetermined pressure in the reaction vessel 31, and carbon monoxide is produced. Nanocarbon adhered to the catalyst is consumed with the progress of the reaction, and a catalyst refreshing step in which refreshing and activation of a catalyst are simultaneously conducted. The catalyst refreshed can be used again in the lower hydrocarbon decomposition reactor. The catalyst refreshed can be returned to the reaction vessel 11 of the lower hydrocarbon decomposition reactor 10 through the nanocarbon-catalyst mixture transfer tube 43 and the nanocarbon collection vessel 42. Carbon monoxide produced in the reaction vessel 31 is transferred to the mixing equipment 50 through the carbon monoxide transfer tube 34.

The hydrogen and carbon monoxide produced as above are supplied to the mixing equipment 50 and mixed therein. A synthesis gas having a predetermined gas ratio is produced by discharging outside a predetermined amount of hydrogen. A synthesis gas having a predetermined gas ratio may be produced by adjusting the amounts of hydrogen and carbon monoxide supplied to the mixing equipment 50. The synthesis gas produced is transferred outside the mixing equipment 50 through the synthesis gas transfer tube 51. The synthesis gas transferred through the synthesis gas transfer tube 51 may be directly supplied to a synthesis step for producing methanol and the like, or may be once stored in a bomb or the like. The synthesis gas is desirably directly supplied to the synthesis step in order to effectively utilize high temperature heat of the synthesis gas.

Excess hydrogen in the mixing equipment 50 is transferred from the mixing equipment 50 through the excess hydrogen transfer tube 52, and can be appropriately utilized, or can be discarded.

A gas ratio of the synthesis gas can be selected depending on the kind of a material to be produced based on the synthesis gas, a production method, and the like. For example, in the case of producing methanol based on the synthesis gas, the ratio between carbon monoxide and hydrogen is theoretically preferably 1:2.

Embodiment 2

Figure 2:
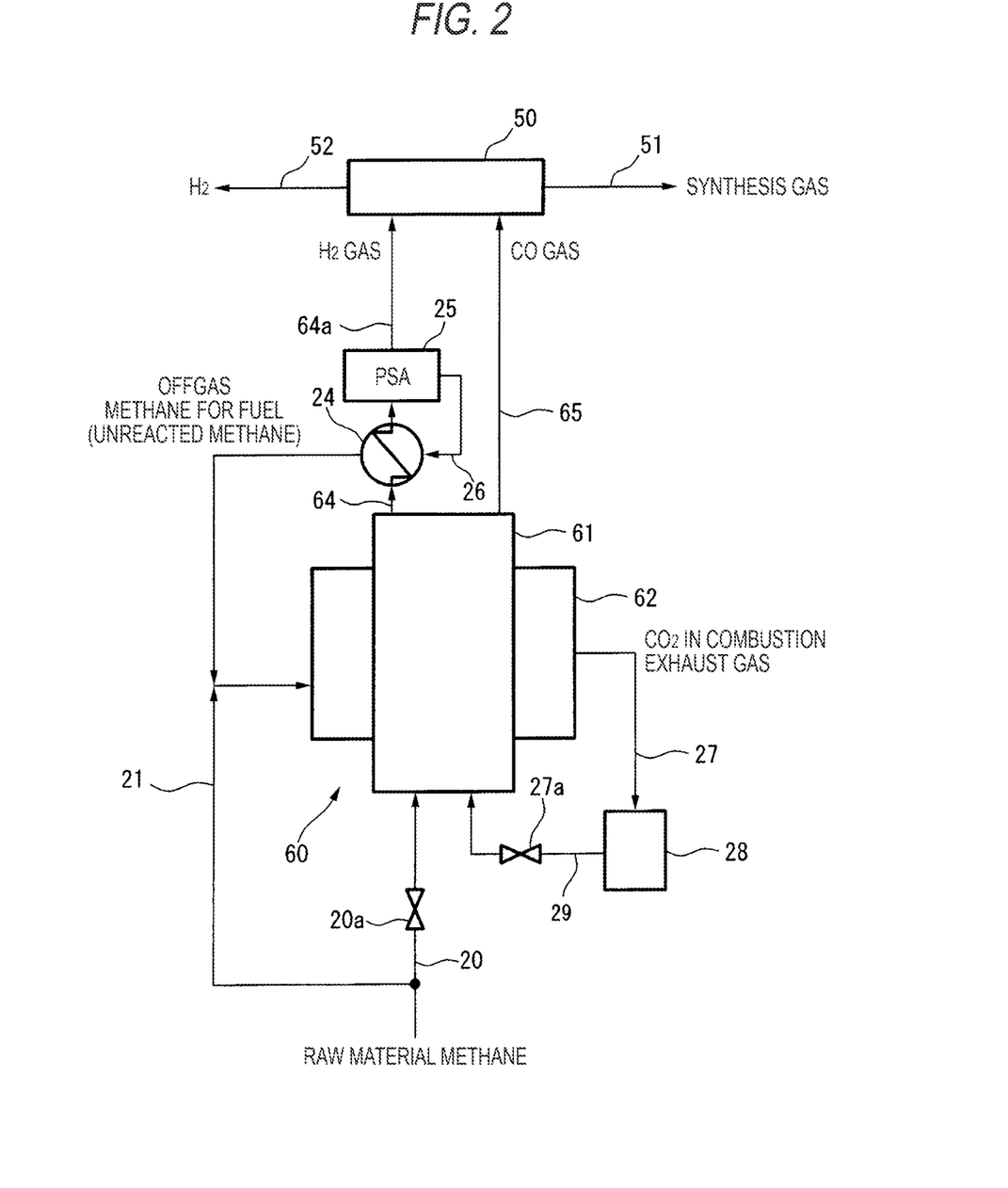
FIG. 2 is a schematic view showing another embodiment of the synthesis gas and nanocarbon production system in the present invention.

Another embodiment is described below based on FIG. 2.

In the embodiment 2, a reaction space for conducting lower hydrocarbon decomposition and a reaction space for conducting carbon dioxide reduction reaction are united, and lower hydrocarbon decomposition and carbon dioxide reduction are conducted in one reaction vessel. In the embodiment 2, the same constitutions as in the embodiment 1 have the same reference numerals, and their explanations are omitted or simplified.

The production system of the present invention includes a reactor 60 and a mixing equipment 50. The reactor 60 includes a reaction vessel 61 and a furnace 62 for heating the reactor 61 by surrounding the reaction vessel 61. A catalyst for directly decomposing lower hydrocarbon is stored in the reaction vessel 61. A lower hydrocarbon supply tube 20 for supplying methane as a raw material and a carbon dioxide supply tube 27 for supplying carbon dioxide are connected to the reaction vessel 61. An on-off valve 20a is provided in the lower hydrocarbon supply tube 20, and an on-off valve 27a is provided in the carbon dioxide supply tube 27, thereby making it possible to selectively supply hydrogen and carbon dioxide to the reaction vessel 61. Therefore, in this embodiment, the on-off valves 20a and 27a correspond to the switching parts of the present invention.

A fuel supply tube 21 for supplying methane as a fuel to the furnace 62 is connected to the furnace 62, and the fuel supply tube 21 is branched and connected to the lower hydrocarbon supply tube 20. One end of the carbon dioxide supply tube 27 for discharging carbon dioxide in the exhaust gas generated by combustion in the furnace 62 outside the furnace is connected to the furnace 62, a carbon dioxide storage tank 28 and the on-off valve 27a are sequentially provided in the carbon dioxide supply tube 27, and the carbon dioxide supply tube 27 is connected to the reaction vessel 61 as described before.

An production gas transfer tube 64 for transferring production gas produced in the reaction vessel 61 in the lower hydrocarbon decomposition step is connected to the reaction vessel 61, and the production gas transfer tube 64 is connected to a PSA 25 through a heat exchanger 24. A return flow tube 26 for transferring methane separated and collected, and a hydrogen transfer tube 64a for transferring hydrogen separated from the production gas are connected to the PSA 25. Another end of the hydrogen transfer tube 64a is connected to the mixing equipment 50. The return flow tube 26 joins the fuel transfer tube 21 through the heat exchanger 24.

A carbon monoxide transfer tube 65 for transferring carbon monoxide produced in the reaction vessel 61 in the carbon dioxide reduction step is connected to the reaction vessel 61, and another end of the carbon monoxide transfer tube 65 is connected to the mixing equipment 50.

Action of this embodiment is described below.

In the initial state, the on-off valve 20a of the lower hydrocarbon supply tube 20 is opened, and an on-off valve of the carbon dioxide supply tube 27 is closed, making it possible to supply methane to the reaction vessel 61.

The reaction vessel 61 is heated by the furnace 62 using methane as a fuel supplied through the fuel supply tube 21. In this case, a part or the whole of the carbon dioxide in the combustion exhaust gas discharged from the furnace 62 is temporarily stored in the carbon dioxide storage tank 28 provided in the carbon dioxide supply tube 27. This reduces the amount of carbon dioxide discharged outside.

The production gas produced in the reaction vessel 61 is discharged outside the reaction vessel 61 through the production gas transfer tube 64 and transferred to the PSA 25 through the heat exchanger 24.

The production gas is separated into unreacted methane and hydrogen by the PSA 25, and the methane collected is transferred to the fuel supply tube 21 through the heat exchanger 24 by the return flow tube 26 and can be used again as a fuel. Heat exchange between the production gas and the methane collected is performed in the heat exchanger 24, the production gas is cooled, and at the same time, the methane collected is heated. The hydrogen separated by the PSA 25 is transferred to the mixing equipment 50 through the hydrogen transfer tube 64a.

Nanocarbon is produced in the reaction vessel 61 by the decomposition reaction described before.

After passing a predetermined period of time, the on-off valve 20a is closed, the on-off valve 27a is opened, and carbon dioxide is supplied to the reaction vessel 61 through a carbon dioxide supply tube 29. In this case, a sufficient amount of carbon dioxide is supplied through the carbon dioxide storage tank 28. The temperature of the furnace 62 is appropriately adjusted by, for example, adjusting an amount of a fuel supplied, as necessary. The action of the on-off valves 20a and 27a can be conducted by the control by a control part not shown.

In the reaction vessel 61, the lower hydrocarbon decomposition step switches to the carbon dioxide reduction step, nanocarbon and carbon dioxide present in the reaction vessel 61 are reacted to produce carbon monoxide. In this case, nanocarbon adhered to the catalyst is consumed with the progress of reaction, and a catalyst refreshing step that performs refreshing and activation of a catalyst is simultaneously conducted.

A part of nanocarbon before the reaction may be extracted before initiating the carbon dioxide reduction reaction.

The carbon monoxide produced is transferred to the mixing equipment 50 through the carbon monoxide transfer tube 65.

The hydrogen and carbon monoxide produced as above are supplied to the mixing equipment 50 and mixed therein, thereby producing a synthesis gas having a predetermined gas ratio. The synthesis gas having a desired gas ratio can be obtained by adjusting the amounts of hydrogen and carbon monoxide supplied to the mixing equipment 50.

After passing a predetermined time, the on-off valve 20a is opened, the on-off valve 27a is closed, and methane is supplied to the reaction vessel 61 through the lower hydrocarbon supply tube 20. The temperature of the furnace 62 is appropriately adjusted by, for example, adjusting the amount of a fuel supplied, as necessary. The predetermined time can differ from the predetermined time for switching to the carbon dioxide reduction step from the lower hydrocarbon decomposition step.

In the reaction vessel 61, the carbon dioxide reduction step switches to the lower hydrocarbon decomposition step, decomposition reaction of methane by the catalyst occurs in the reaction vessel 61, thereby hydrogen and nanocarbon are produced, and the production of the synthesis gas is conducted together with the production of nanocarbon.

Thus, the lower hydrocarbon decomposition reaction and the carbon dioxide reduction step can be conducted in one reaction vessel by switching the supply of lower hydrocarbon and the supply of carbon dioxide, and a synthesis gas and nanocarbon can be finally produced.

An interval for switching the supply of lower hydrocarbon and the supply of carbon dioxide can be appropriately determined depending on necessary amounts of hydrogen and carbon monoxide, reaction conditions, and the like.

Although the present invention has been described based on the above each embodiment, the invention is not limited to the contents of the above embodiments, and modifications or changes can be appropriately made without departing the scope of the present invention.

EXAMPLE

Figure 1:
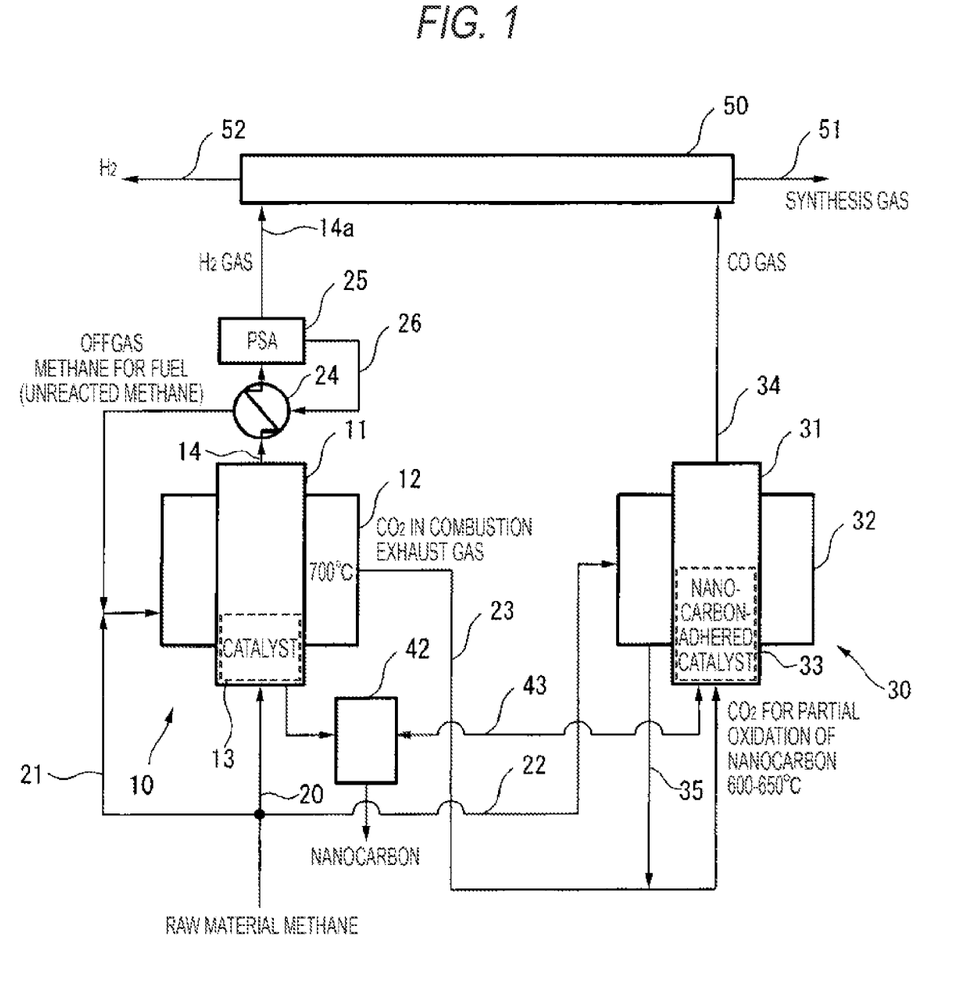
FIG. 1 is a schematic view showing one embodiment of the synthesis gas and nanocarbon production system in the present invention.
Figure 3:
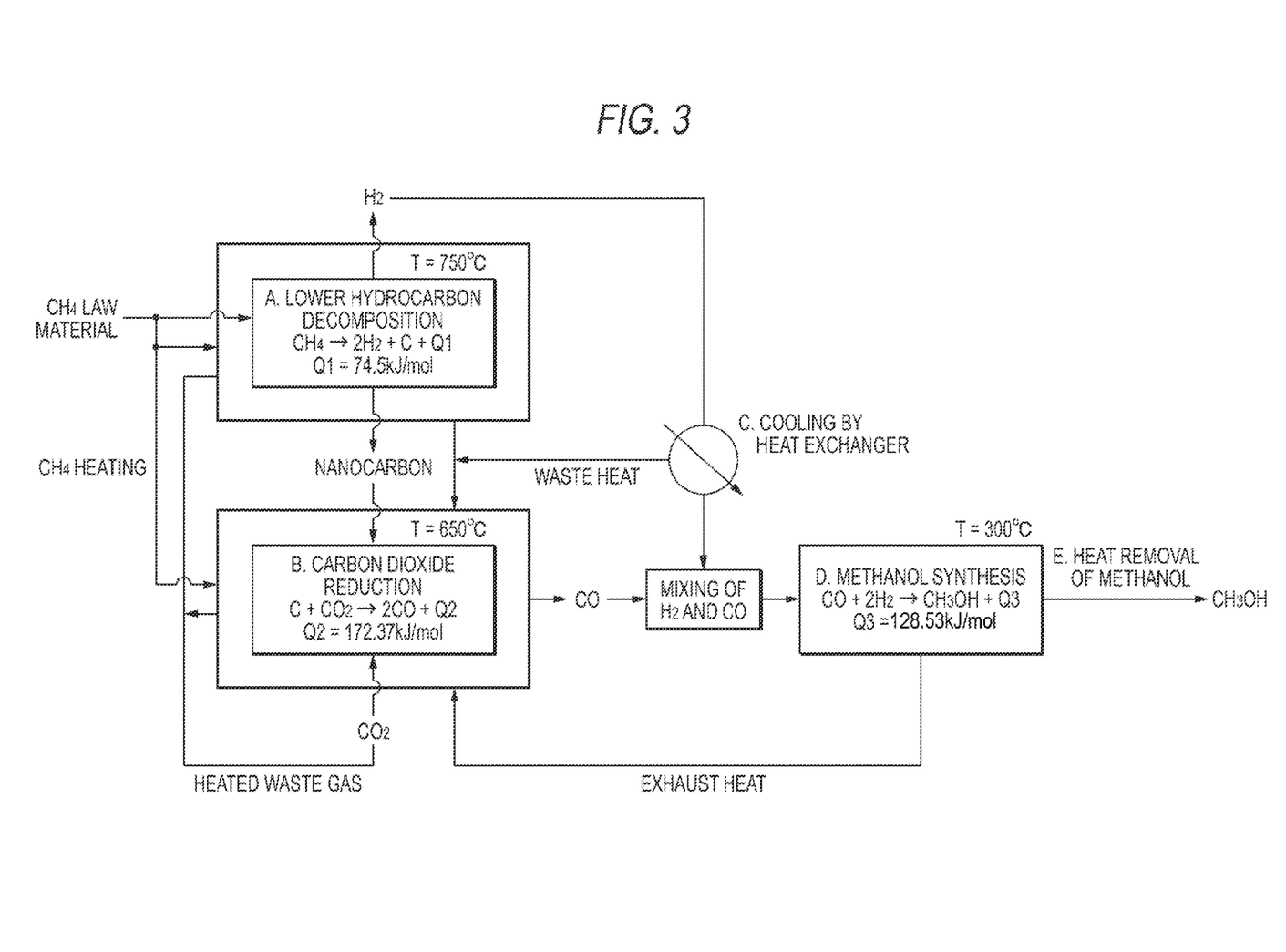
FIG. 3 is a view showing a process flow of examples in which a synthesis gas and nanocarbon are synthesized using methane as a raw material and methanol is synthesized from the synthesis gas.

One example of a step of producing a synthesis gas and nanocarbon from methane and carbon dioxide using the production system shown in FIG. 1 and producing methanol based on the synthesis gas is described based on the process flow of FIG. 3.

Reaction conditions and material balance in each stage of A. Lower hydrocarbon decomposition, B. Carbon dioxide reduction, C. Cooling by heat exchanger, D. Methanol synthesis reaction, and E. Heat removal of methanol in FIG. 3 are shown in Table 1. This example is based on the assumption that waste heat in producing methanol based on the synthesis gas produced, and waste heat in removing heat of the methanol are reutilized in the reaction step. The catalyst is a catalyst containing alumina and 30 mass % of iron supported thereon in the lower hydrocarbon decomposition step, and is a catalyst in which copper oxide (CuO) is used as an active metal, in the methanol synthesis reaction step. Methanol synthesis can use a catalyst in which Cu, Zn or an alloy containing at least one of Cu and Zn is used as an active metal.

Methanol just after produced has a temperature of 300° C. The methanol is subjected to heat removal to have a temperature of 20° C. Heat obtained by the heat removal can be utilized as heat source in other steps.

Material balance in this example is described based on Table 1.

TABLE 1

|  |  | A. Lower hydrocarbon decomposition | B. Carbon dioxide reduction | C. Cooling by heat exchanger* | D. Methanol synthesis reaction** | E. Heat removal of methanol*** |
|---|---|---|---|---|---|---|
| Temperature | (° C.) | 750 | 650 | 300 | 300 | 20 |
| Amount of necessary heat for reaction | (kJ) | 7,648 | 6,583 | −1,560 | −1,845 | −1,751 |
| Amount of heat corresponding to necessary fuel | (kJ) | 15,296 | 13,166 | −1,560 | −1,845 | −1,751 |
| Amount of fuel $CH_4$ | (mol) | 19.04 | 16.39 | −1.94 | −2.30 | −2.18 |
| Pressure | (MPaG) | 0.10 | 0.10 | 0.10 | 3.00 | 0.10 |
| Total number of moles | (mol) | 60.00 | 210.00 | 120.00 | 180.00 | 60.00 |
| $CH_4$ |  | 60.00 | 0.00 | 0.00 | 0.00 | 0.00 |
| $H_2$ |  | 0.00 | 120.00 | 120.00 | 120.00 | 0.00 |
| Nanocarbon |  | 0.00 | 60.00 | 0.00 | 0.00 | 0.00 |
| $CO_2$ |  | 0.00 | 30.00 | 0.00 | 0.00 | 0.00 |
| CO |  | 0.00 | 0.00 | 0.00 | 60.00 | 0.00 |
| $CH_3OH$ |  | 0.00 | 0.00 | 0.00 | 0.00 | 60.00 |

Furnace efficiency 50%
Amount of fuel $CH_4$ 29.02 mol
Discharged amount of fuel $CO_2$ 29.02 mol
*Heat removal amount is such that 120 mol of hydrogen is cooled from 750° C. to 300° C.
**Because this is an exothermic reaction, reaction heat is utilized
***Heat removal amount is such that 60 mol of methanol is cooled from 300° C. to 20° C.

60 mol of raw material methane is supplied to the reaction vessel 11 of the lower hydrocarbon decomposition reactor 10, and the furnace 12 is heated to 750° C. by fuel methane. As a result, 120 mol of hydrogen and 60 mol of nanocarbon are produced by the following reaction (A. Lower hydrocarbon decomposition).

$$CH_4 \rightarrow 2H_2 + C + Q1 \quad (Q1=74.5 \text{ kJ/mol})$$

Carbon dioxide is discharged as a combustion exhaust gas. Reaction heat in the lower hydrocarbon decomposition reaction in this case can be utilized as heat source for the carbon dioxide reduction step. The hydrogen produced in the above reaction has high temperature as 750° C., and the hydrogen is cooled to 300° C. by a heat exchanger (C. Cooling by heat exchanger).

Waste heat obtained by the heat exchanger is utilized as heat source for the carbon dioxide reduction step.

30 mol of the nanocarbon produced above and 30 mol of the carbon dioxide are supplied to a reaction vessel of a carbon monoxide production reactor, and a furnace is heated to 650° C. by fuel methane. As a result, 60 mol of carbon monoxide is produced by the following reaction (B. Carbon dioxide reduction).

$$C + CO_2 \rightarrow 2CO + Q2 \quad (Q2=172.37 \text{ kJ/mol})$$

When 60 mol of carbon monoxide produced and 120 mol of hydrogen produced are mixed in a mixing equipment, 180 mol of a synthesis gas having a ratio of carbon monoxide to hydrogen of 1:2 is produced. When reaction is conducted at a reaction temperature of 300° C. using 180 mol of the synthesis gas, 60 mol of methanol can be produced (D. Methanol synthesis reaction). The reaction for producing methanol from the synthesis gas is an exothermic reaction. Therefore, reaction heat can be utilized as heat source.

$$CO + 2H_2 \rightarrow CH_3OH + Q3 \quad (Q3=128.53 \text{ kJ/mol})$$

When methane is used as a fuel and furnace efficiency is assumed to be 50%, the amount of carbon dioxide discharged by combustion of a fuel is theoretically about 30 mol, as shown in Table 1. When a synthesis gas is produced using all of the carbon dioxide discharged and methanol is synthesized from the synthesis gas, it is possible that the amount of carbon dioxide finally discharged in this example is zero.

Although the present invention has been described in detail and by reference to the specific embodiments, it is apparent to one skilled in the art that various modifications or changes can be made without departing from the spirit and scope of the present invention. This application is based on Japanese Patent Application No. 2011-053865 filed Mar. 11, 2011, the disclosure of which is incorporated herein by reference.

REFERENCE SIGNS LIST

10 Lower hydrocarbon decomposition reactor
11 Reaction vessel
12 Furnace
14 Production gas transfer tube
14a Hydrogen transfer tube
20 Lower hydrocarbon supply tube
20a On-off valve
21 Fuel supply tube
22 Fuel supply tube
23 Carbon dioxide supply tube
24 Heat exchanger
27 Carbon dioxide supply tube
27a On-off valve
28 Carbon dioxide storage tank
29 Carbon dioxide supply tube
30 Carbon monoxide production reactor
31 Reaction vessel
32 Furnace 34 Carbon monoxide transfer tube
35 Carbon dioxide supply tube
42 Nanocarbon collection vessel
43 Nanocarbon-catalyst mixture transfer tube
50 Mixing equipment
60 Reactor
61 Reaction vessel
62 Furnace
64 Production gas transfer tube
64a Hydrogen transfer tube
65 Carbon monoxide transfer tube

The invention claimed is:

1. A synthesis gas and nanocarbon production method, comprising:
- a lower hydrocarbon decomposition step of directly decomposing lower hydrocarbon using a catalyst to produce hydrogen and nanocarbon;
- a carbon dioxide reduction step of reacting a part of the nanocarbon produced in the lower hydrocarbon decomposition step with carbon dioxide to produce carbon monoxide; and
- a mixing step of mixing the hydrogen produced in the lower hydrocarbon decomposition step and the carbon monoxide produced in the carbon dioxide reduction step in a predetermined ratio to obtain a synthesis gas.

2. The synthesis gas and nanocarbon production method according to claim 1, further comprising a synthesis step of subjecting the synthesis gas obtained in the mixing step to a reaction to obtain a synthetic substance.

3. The synthesis gas and nanocarbon production method according to claim 1, wherein the carbon dioxide reduction step includes a catalyst refreshing step of subjecting a part or the whole of the catalyst used in the lower hydrocarbon decomposition step to the reaction between the nanocarbon and the carbon dioxide, and removing a part or the whole of the nanocarbon produced in the lower hydrocarbon decomposition step from the catalyst in conducting the reaction.

4. The synthesis gas and nanocarbon production method according to claim 3, wherein the catalyst refreshed in the catalyst refreshing step is again applied to the lower hydrocarbon decomposition step.

5. The synthesis gas and nanocarbon production method according to claim 1, wherein the lower hydrocarbon contains methane.

6. The synthesis gas and nanocarbon production method according to claim 1, wherein the catalyst comprises at least one of nickel and iron, supported on at least one of alumina, silica, magnecia, calcia, hydrotalcite, and carbon.

7. The synthesis gas and nanocarbon production method according to claim 1, wherein the carbon dioxide is collected from at least one of combustion exhaust gas in the lower hydrocarbon decomposition step, exhaust gas in various industries, and biogas.

8. The synthesis gas and nanocarbon production method according to claim 1, wherein at least one of lower hydrocarbon and hydrogen is used as a reducing agent in the carbon dioxide reduction step.

9. The synthesis gas and nanocarbon production method according to claim 1, wherein the lower hydrocarbon decomposition step and the carbon dioxide reduction step are conducted by switching supply of the lower hydrocarbon and supply of the carbon dioxide to the same catalyst.

10. The synthesis gas and nanocarbon production method according to claim 1, further comprising:
- a collection step for collecting the nanocarbon produced in the lower hydrocarbon decomposition step,
- wherein the nanocarbon collected in the collection step is supplied to the carbon dioxide reduction step.

11. The synthesis gas and nanocarbon production method according to claim 10, wherein after pulverizing the nanocarbon collected together with the catalyst in the collection step, high purity carbon and nanocarbon containing high concentration of the catalyst are separated by at least one of specific gravity and magnetism, and the nanocarbon containing high concentration of the catalyst is preferentially supplied to the carbon dioxide reduction step.

12. The synthesis gas and nanocarbon production method according to claim 1,
- wherein the lower hydrocarbon decomposition step comprises while heating a vessel accommodating the catalyst by a furnace that uses the lower hydrocarbon as a fuel, supplying the lower hydrocarbon to the heated vessel so as to decompose the lower hydrocarbon by using the catalyst to produce the hydrogen and the nanocarbon, and
- wherein the carbon dioxide reduction step comprises reacting the part of the nanocarbon produced in the lower hydrocarbon decomposition step with the carbon dioxide that is collected from combustion exhaust gas in the lower hydrocarbon decomposition step to produce the carbon monoxide.

13. The synthesis gas and nanocarbon production method according to claim 12,
- wherein the lower hydrocarbon decomposition step further comprises:
  - discharging exhaust gas containing unreacted lower hydrocarbon and the hydrogen from the vessel; and
  - separating the unreacted lower hydrocarbon and the hydrogen from the exhaust gas so as to transfer the hydrogen to a mixing part and to return the unreacted lower hydrocarbon to be used again as the fuel, and
- wherein the carbon dioxide reduction step further comprises transferring the carbon monoxide to the mixing part, and
- wherein the mixing step comprise mixing the hydrogen produced in the lower hydrocarbon decomposition step and the carbon monoxide produced in the carbon dioxide reduction step in a predetermined ratio in the mixing part to obtain the synthesis gas.

* * * * *